United States Patent
Hudson

(10) Patent No.: US 7,563,239 B1
(45) Date of Patent: Jul. 21, 2009

(54) EAR EXFOLIATING SWAB SYSTEM

(76) Inventor: Donald E. Hudson, Gulfport, FL (US); Rebecca W. Hudson, legal representative, 6217 Vista Verde Dr. W., Gulfport, FL (US) 33707

( * ) Notice: Subject to any disclaimer, the term of this patent is extended or adjusted under 35 U.S.C. 154(b) by 292 days.

(21) Appl. No.: 11/515,272

(22) Filed: Sep. 1, 2006

Related U.S. Application Data

(60) Provisional application No. 60/714,083, filed on Sep. 2, 2005.

(51) Int. Cl.
*A61M 35/00* (2006.01)

(52) U.S. Cl. .......................... 604/1; 15/244.1
(58) Field of Classification Search ................. 604/1–3; 15/244.1
See application file for complete search history.

(56) References Cited

U.S. PATENT DOCUMENTS

| | | | | |
|---|---|---|---|---|
| 355,308 A | * | 1/1887 | Foote | 604/93.01 |
| 1,652,108 A | * | 12/1927 | Forbis | 604/1 |
| 1,688,374 A | * | 10/1928 | Belfry | 15/227 |
| 2,495,237 A | * | 1/1950 | Petiton | 106/122 |
| 2,510,961 A | * | 6/1950 | Davis | 604/1 |
| 2,544,216 A | * | 3/1951 | Brackmann | 15/222 |
| 2,842,799 A | * | 7/1958 | Politzer | 264/49 |
| 3,179,108 A | * | 4/1965 | Bloch et al. | 604/1 |
| 3,352,307 A | * | 11/1967 | Bloxham | 604/1 |
| 3,586,380 A | * | 6/1971 | Alibeckoff | 300/21 |
| 3,724,018 A | * | 4/1973 | Sills | 15/244.1 |
| 4,718,889 A | * | 1/1988 | Blasius et al. | 604/1 |
| 4,820,259 A | | 4/1989 | Stevens | |
| 4,935,001 A | * | 6/1990 | George | 604/1 |
| 5,107,861 A | * | 4/1992 | Narboni | 128/864 |
| 5,158,532 A | * | 10/1992 | Peng et al. | 604/1 |
| 5,241,714 A | | 9/1993 | Barry | |
| 5,715,559 A | * | 2/1998 | Mitri | 15/118 |
| 5,715,850 A | * | 2/1998 | Markgraaf | 132/333 |
| 5,915,434 A | | 6/1999 | Juarez | |
| 2003/0000039 A1 | * | 1/2003 | Borcherds | 15/209.1 |
| 2004/0220507 A1 | * | 11/2004 | Blair | 604/1 |
| 2005/0037038 A1 | * | 2/2005 | Gupta | 424/401 |
| 2006/0165741 A1 | * | 7/2006 | Coffindaffer et al. | 424/401 |

* cited by examiner

*Primary Examiner*—Tatyana Zalukaeva
*Assistant Examiner*—Paula L Craig
(74) *Attorney, Agent, or Firm*—Edward P. Dytkiewicz

(57) ABSTRACT

A cylindrical support rod has a first end and a second end with a central length between the ends. A quantity of an exfoliating material is coupled to one end of the rod.

1 Claim, 4 Drawing Sheets

EAR EXFOLIATING SWAB SYSTEM

RELATED APPLICATION

The present application is based upon pending Provisional Patent Application Ser. No. 60/714,083 filed Sep. 2, 2005, the subject matter of which is incorporated herein by reference.

BACKGROUND OF THE INVENTION

1. Field of the Invention

The present invention relates to a ear exfoliating swab system and more particularly pertains to facilitating the removal of dead cells and wax from inside the outer ear to reveal healthy new skin cells and improve circulation throughout the exterior of the ear.

2. Description of the Prior Art

The use of a wide variety of cleaning devices is known in the prior art. More specifically, cleaning devices previously devised and utilized for personal hygiene and a wide variety of additional purposes are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,820,259 issued Apr. 11, 1989 to Stevens relates to an External Ear Cleaning Device. U.S. Pat. No. 5,241,714 issued Sep. 7, 1993 to Barry relates to a Shower Personal Hygiene System. Lastly, U.S. Pat. No. 5,915,434 issued Jun. 19, 1999 to Juarez relates to a Hand-Held Body Washing and Scrubbing Device.

While these devices fulfill their respective objectives and requirements, the aforementioned patents do not describe an ear exfoliating swab system that facilitates the removal of dead cells and wax from inside the outer ear to reveal healthy new skin cells and improve circulation throughout the exterior of the ear.

In this respect, the ear exfoliating swab system according to the present invention substantially departs from the conventional concepts and designs of the prior art, and in doing so provides an apparatus primarily developed for the purpose of facilitating the removal of dead cells and wax from inside the outer ear to reveal healthy new skin cells and improve circulation throughout the exterior of the ear.

Therefore, it can be appreciated that there exists a continuing need for a new and improved ear exfoliating swab system which can be used for facilitating the removal of dead cells and wax from inside the outer ear to reveal healthy new skin cells and improve circulation throughout the exterior of the ear. In this regard, the present invention substantially fulfills this need.

SUMMARY OF THE INVENTION

In view of the foregoing disadvantages inherent in the known types of cleaning devices now present in the prior art, the present invention provides an improved ear exfoliating swab system. As such, the general purpose of the present invention, which will be described subsequently in greater detail, is to provide a new and improved ear exfoliating swab system and method which has all the advantages of the prior art and none of the disadvantages.

To attain this, the present invention essentially comprises an ear exfoliating swab system for facilitating the removal of dead cells and wax from inside the outer ear to reveal healthy new skin cells and improve circulation throughout the exterior of the ear. Such system comprises, in combination, a cylindrical support rod having a circular cross sectional configuration and fabricated of a generally rigid material with limited flexibility and resilience. The rod has a first upper end and an opposed second lower end with a central length along the entire rod between the ends. The central length has a first upper central extent of a smaller diameter and a second lower central extent of a larger diameter. The upper and lower central extents have an essentially common length with a bend of between about 30 and 60 degrees adjacent to a midpoint of the upper central extent and with the lower central extent having a diameter between 2 and 5 times the diameter of the upper central extent.

A quantity of cotton is secured adjacent to the upper end of the rod and has a generally hemispherical region extending upwardly from the upper end with a tapering region adjacent to a length of the rod adjacent to the upper end and extending downwardly from the hemispherical region. The hemispherical region has a radius essentially equal to the diameter of the upper central extent of the rod. The tapering region has a length between about 5 and 10 percent of the length of the rod.

An interior layer of loofah sponge is coupled to the cotton. The interior layer of loofah sponge has a generally hemispherical region overlying the hemispherical region of the cotton and a tapered region overlying the tapered region of the cotton and terminating in a free end.

An exterior layer of loofah sponge is coupled to the interior layer. The exterior layer of loofah sponge has a generally hemispherical region overlying the hemispherical region of the interior layer and a tapered region overlying the tapered region of the interior layer and terminating in a free end. The hemispherical region of each quantity of loofah sponge has a thickness essentially equal to half the thickness hemispherical region of the quantity of cotton. The tapering regions of the quantity of loofah sponge has a length between about 10 and 20 percent of the length of the rod. The interior and exterior layers of loofah sponge and the cotton constitute an exfoliating assembly.

Lastly, a coupling assembly has an inner tube fabricated of a plastic material with limited flexibility and limited resilience and positionable over and frictionally retained on the upper end of the upper end of the rod. The inner tube has a closed end positionable over the upper end of the rod and an open end spaced therefrom. The coupling assembly also has an outer tube fabricated of a plastic material with limited flexibility and limited resilience and positionable over and frictionally retained on the inner tube. The outer tube has a closed end positionable over the closed end of the inner tube and an open end spaced therefrom. The tapering regions of the interior and exterior layers of the loofah sponge are of a length greater than the length of the tubes whereby the free ends of the interior and exterior layers are positionable between the free ends of the tubes prior to positioning the exfoliating assembly on the rod.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ear exfoliating swab system which has all of the advantages of the prior art cleaning devices and none of the disadvantages.

It is another object of the present invention to provide a new and improved ear exfoliating swab system which may be easily and efficiently manufactured and marketed.

It is further object of the present invention to provide a new and improved ear exfoliating swab system which is of durable and reliable constructions.

An even further object of the present invention is to provide a new and improved ear exfoliating swab system which is susceptible of a low cost of manufacture with regard to both materials and labor, and which accordingly is then susceptible of low prices of sale to the consuming public, thereby making such ear exfoliating swab system economically available to the buying public.

Even still another object of the present invention is to provide a ear exfoliating swab system for facilitating the removal of dead cells and wax from inside the outer ear to reveal healthy new skin cells and improve circulation throughout the exterior of the ear.

Lastly, it is an object of the present invention to provide a new and improved ear exfoliating swab system. A cylindrical support rod has a first end and a second end with a central length between the ends. A quantity of an exfoliating material is coupled to one end of the rod.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
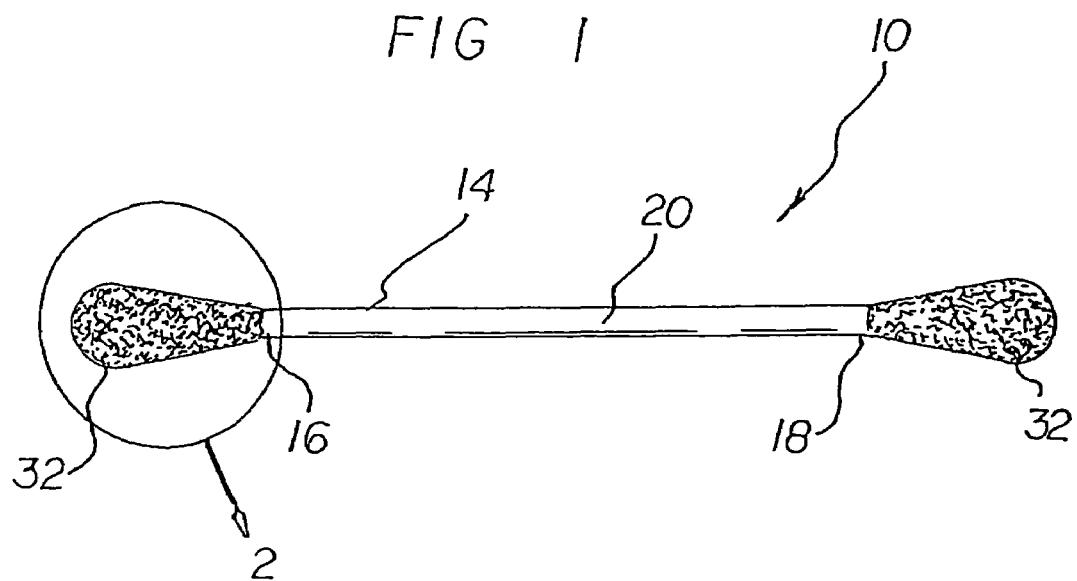
FIG. 1 is a front elevational view of an ear exfoliating swab system constructed in accordance with the principles of the present invention.
Figure 2:
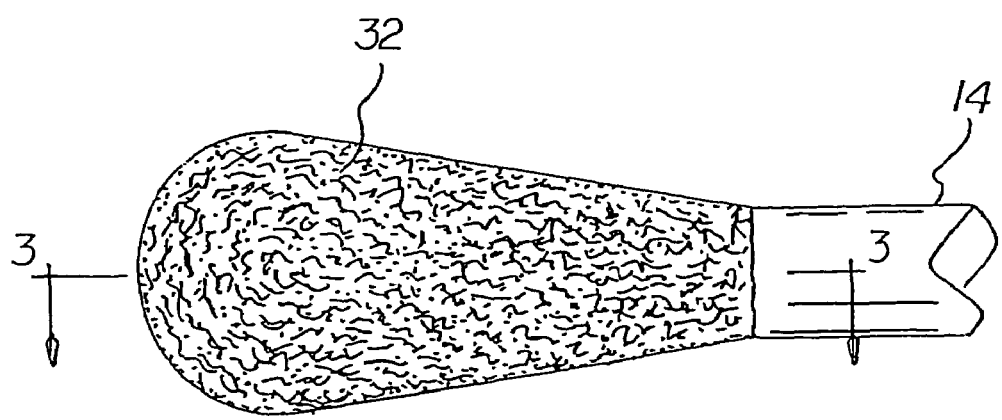
FIG. 2 is an enlarged front elevational view taken at circle 2 of FIG. 1.
Figure 3:
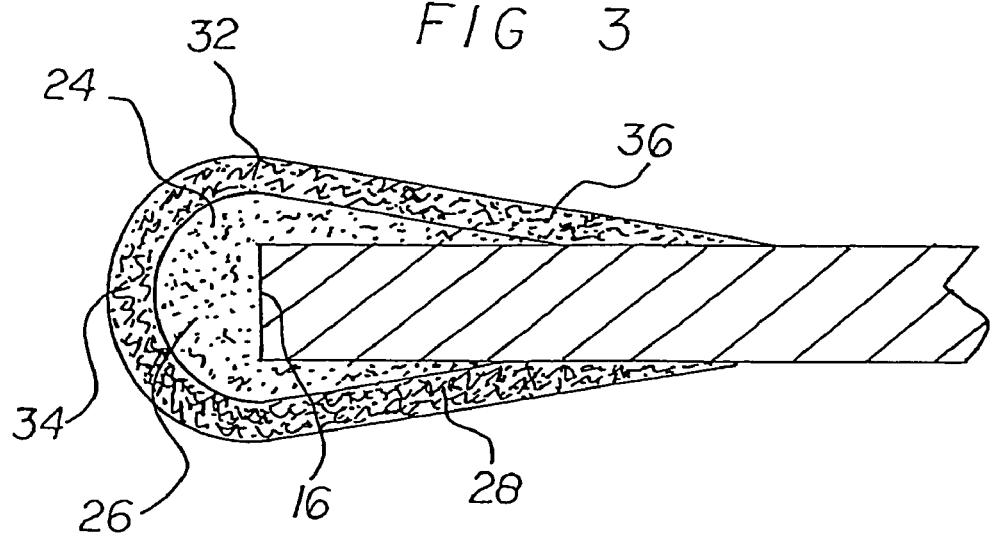
FIG. 3 is a cross sectional view taken at line 3-3 of FIG. 1.

With reference now to the drawings, and in particular to FIG. 1 thereof, the preferred embodiment of the new and improved ear exfoliating swab system embodying the principles and concepts of the present invention and generally designated by the reference numeral 10 will be described.

The present invention, the ear exfoliating swab system 10 is comprised of a plurality of components. Such components in their broadest context include a cylindrical support rod and a quantify of exfoliating material. Such components are individually configured and correlated with respect to each other so as to attain the desired objectives.

First provided is a cylindrical support rod 14. The rod has a circular cross sectional configuration. The rod has a fixed diameter. The rod is fabricated of a generally rigid material with limited flexibility and resilience. The rod is about three inches in length. The rod has a first end 16. The rod has an opposed similarly configured second end 18. The rod has a central length 20. The central length is provided along the entire of the rod between the ends.

A quantity of cotton 24 is provided. The cotton is secured to each end of the rod. Each quantity of cotton has a generally hemispherical region 26. The hemispherical region extends from an associated end. Each quantity of cotton has a tapering region 28. The tapering region contacts a length of the rod adjacent to the associated end. The hemispherical region has a radius. The radius is essentially equal to the diameter of the rod. The tapering region has a length. The length is between about 5 and 10 percent of the length of the rod.

Provided last is a quantity of loofah sponge 32. The loofah sponge is coupled to each end of the rod. The quantity of loofah sponge has a generally hemispherical region 34. The hemispherical region extends from an associated quantity of cotton at an associated end of the rod. Each quantity of loofah sponge also has a tapering region 36. The tapering region contacts the tapering region of the quantity of cotton. The tapering region also contacts a length of the rod adjacent to the associated end of the rod. The hemispherical region of the quantity of loofah sponge has a thickness. The thickness is essentially equal to half the thickness of the hemispherical region of the quantity of cotton. The tapering region of the quantity of loofah sponge has a length. The length is between about 10 and 20 percent of the length of the rod.

Figure 4:
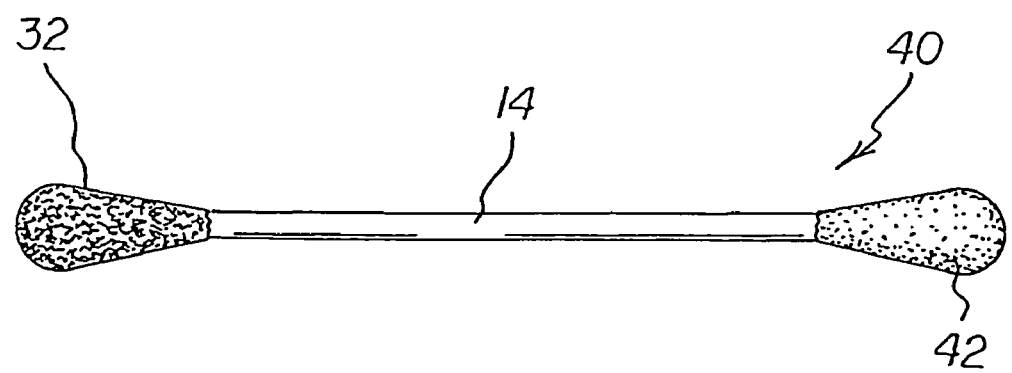
FIG. 4 is front elevational view of an ear exfoliating swab system constructed in accordance with an alternate embodiment of the present invention.

The alternate embodiment of the invention may be seen in FIG. 4. The exfoliating material is coupled to, and exposed at, only at one of the rod. The exfoliating material further includes a quantity of cotton 42. The cotton is attached to, and exposed at, the end of the rod opposite from the exfoliating material.

Loofah sponge is the preferred material for the exterior layer which functions as an exfoliating layer. Cotton is the preferred material for the interior layer which functions as a backing layer. The surface of the exterior layer is preferably a more abrasive surface than the surface of the interior layer.

Figure 5:
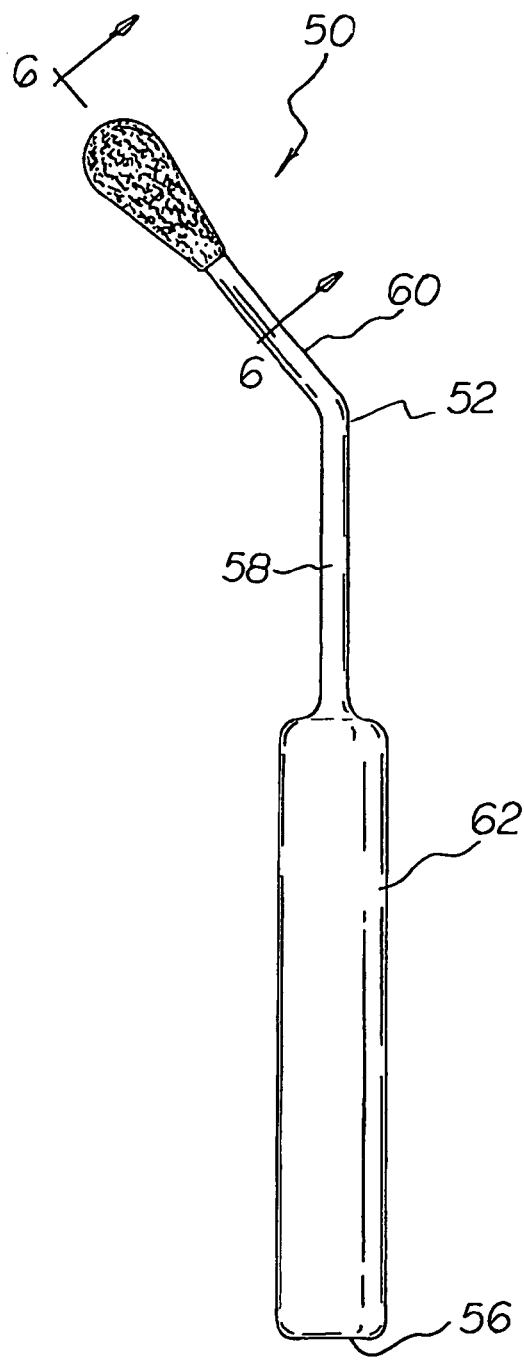
FIG. 5 is a front elevational view of another ear exfoliating swab system constructed in accordance with the principles of the present invention.
Figure 6:
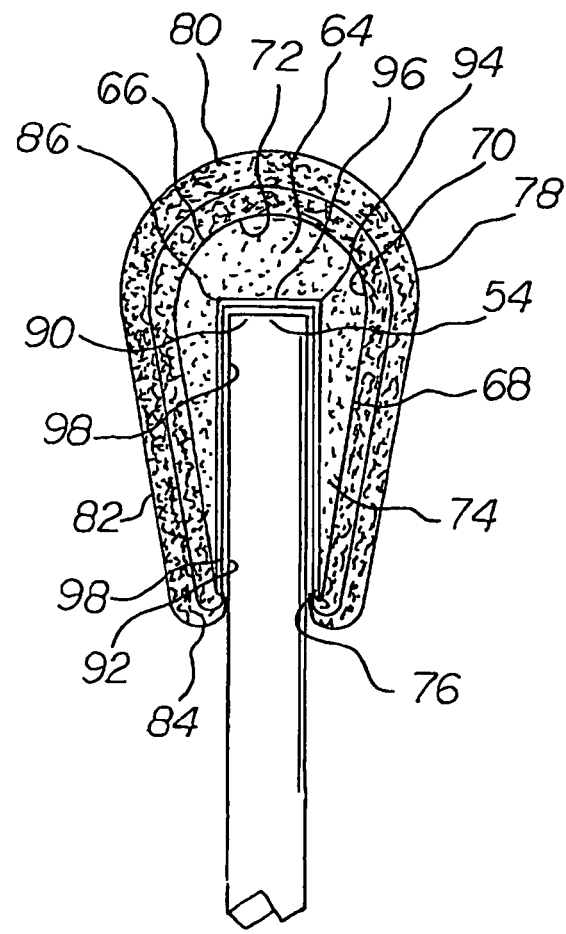
FIG. 6 is a cross sectional view taken at line 6-6 of FIG. 5.
Figure 7:
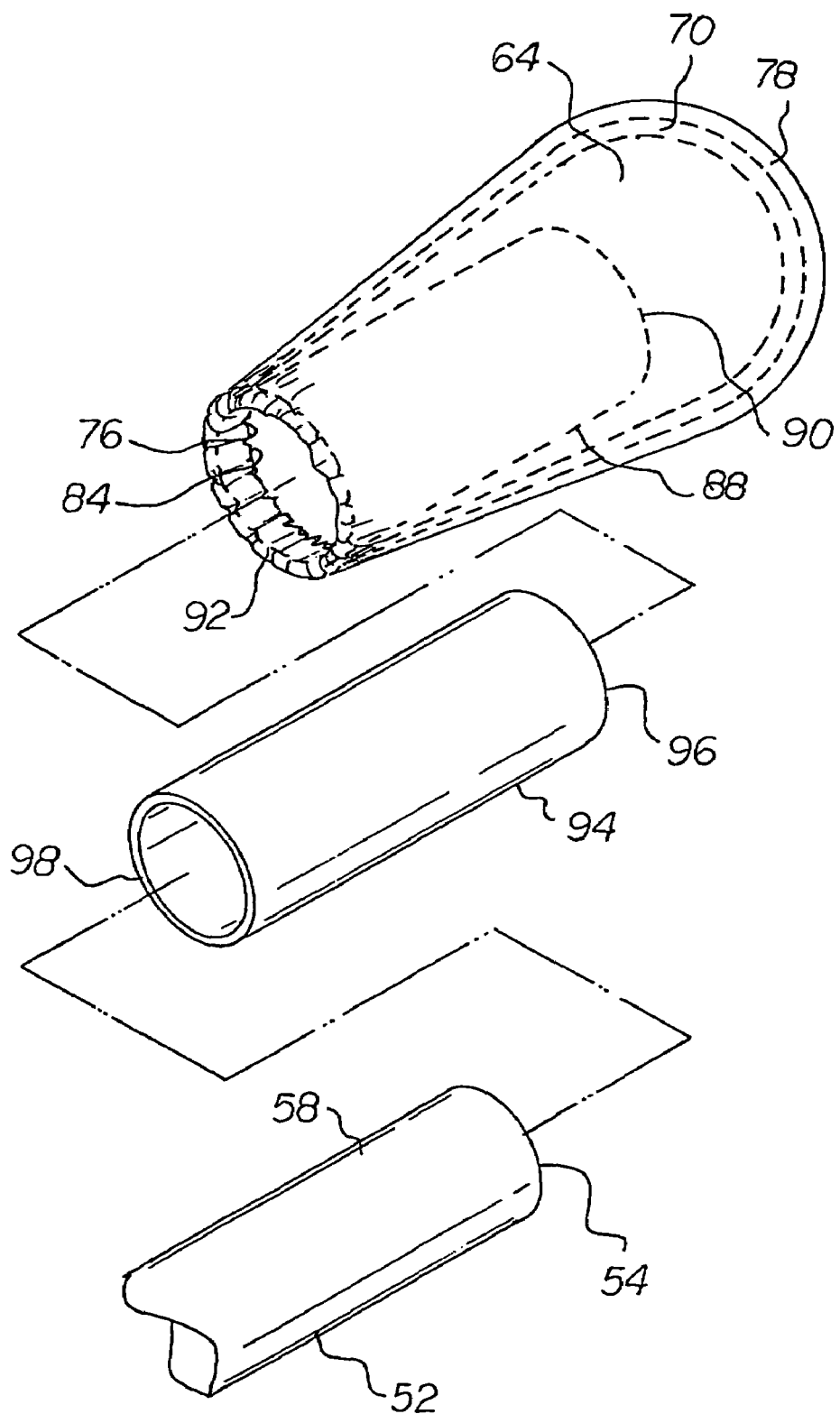
FIG. 7 is an exploded perspective illustration of the system illustrated in FIGS. 5 and 6.

FIGS. 5, 6 and 7 illustrate another embodiment of the invention. In such embodiment there is provided an ear exfoliating swab system 50 for facilitating the removal of dead cells and wax from inside the outer ear to reveal healthy new skin cells and improve circulation throughout the exterior of the ear. Such system comprises, in combination, a cylindrical support rod 52 having a circular cross sectional configuration and fabricated of a generally rigid material with limited flexibility and resilience. The rod has a first upper end 54 and an opposed second lower end 56 with a central length 58 along the rod between the ends. The central length has a first upper central extent 60 of a smaller diameter and a second lower central extent 62 of a larger diameter. The upper and lower central extents have an essentially common length with a bend of between about 30 and 60 degrees adjacent to a midpoint of the upper central extent and with the lower central extent having a diameter between 2 and 5 times the diameter of the upper central extent.

A quantity of cotton 64 is secured adjacent to the upper end of the rod and has a generally hemispherical region 66 extending upwardly from the upper end with a tapering region 68 adjacent to a length of the rod adjacent to the upper end and extending downwardly from the hemispherical region. The hemispherical region has a radius essentially equal to the diameter of the upper central extent of the rod. The tapering region have a length between about 5 and 10 percent of the length of the rod.

In interior layer of loofah sponge 70 is coupled to the cotton. The interior layer of loofah sponge has a generally hemispherical region 72 overlying the hemispherical region of the cotton and a tapered region 74 overlying the tapered region of the cotton and terminating in a free end 76.

An exterior layer of loofah sponge 78 is coupled to the interior layer. The exterior layer of loofah sponge has a generally hemispherical region 80 overlying the hemispherical region of the interior layer and a tapered region 82 overlying the tapered region of the interior layer and terminating in a free end 84. The hemispherical region of each layer of loofah sponge has a thickness essentially equal to half the thickness hemispherical region of the quantity of cotton. The tapering regions of the quantity of loofah sponge have a length between about 10 and 20 percent of the length of the rod. The interior and exterior layers of loofah sponge and the cotton constituting an exfoliating assembly 84.

Lastly, a coupling assembly 86 has an inner tube 88 fabricated of a plastic material with limited flexibility and limited resilience and positionable over and frictionally retained on the upper end of the upper end of the rod. The inner tube has a closed end 90 positionable over the upper end of the rod and an open end 92 spaced therefrom. The coupling assembly also has an outer tube 94 fabricated of a plastic material with limited flexibility and limited resilience and positionable over and frictionally retained on the inner tube. The outer tube has a closed end 96 positionable over the closed end of the inner tube and an open end 98 spaced therefrom. The tapering regions of the interior and exterior layers of the loofah sponge are of a length greater than the length of the tubes. In this manner, the free ends of the interior and exterior layers are positionable between the free ends of the tubes prior to positioning the exfoliating assembly on the rod prior to use.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ear exfoliating swab system for facilitating the removal of dead cells and wax from inside the outer ear to reveal healthy new skin cells and improve circulation throughout the exterior of the ear comprising, in combination:

a cylindrical support rod having a circular cross sectional configuration and fabricated of a generally rigid material with limited flexibility and resilience, the rod having a first upper end and an opposed second lower end with a central length along the entire rod between the ends, the central length having a first upper central extent of a smaller diameter and a second lower central extent of a larger diameter, the upper and lower central extents having an essentially common length with a bend of between about 30 and 60 degrees adjacent to a midpoint of the upper central extent and with the lower central extent having a diameter between 2 and 5 times the diameter of the upper central extent;

a quantity of cotton secured adjacent to the upper end of the rod and having a generally hemispherical region extending upwardly from the upper end with a tapering region adjacent to a length of the rod adjacent to the upper end and extending downwardly from the hemispherical region, the hemispherical region having a radius essentially equal to the diameter of the upper central extent of the rod, the tapering region having a length between about 5 and 10 percent of the length of the rod;

an interior layer of loofah sponge coupled to the cotton, the interior layer of loofah sponge having a generally hemispherical region overlying the hemispherical region of the cotton and a tapered region overlying the tapered region of the cotton and terminating in a free end;

an exterior layer of loofah sponge coupled to the interior layer, the exterior layer of loofah sponge having a generally hemispherical region overlying the hemispherical region of the interior layer and a tapered region overlying the tapered region of the interior layer and terminating in a free end, the hemispherical region of each quantity of loofah sponge having a thickness essentially equal to half the thickness hemispherical region of the quantity of cotton, the tapering regions of the quantity of loofah sponge having a length between about 10 and 20 percent of the length of the rod, the interior and exterior layers of the loofah sponge and the cotton constituting an exfoliating assembly; and a coupling assembly having an inner tube fabricated of a plastic material with limited flexibility and limited resilience and positionable over and frictionally retained on the upper end of the upper end of the rod, the inner tube having a closed end positionable over the upper end of the rod and an open end spaced therefrom, the coupling assembly also having an outer tube fabricated of a plastic material with limited flexibility and limited resilience and positionable over and frictionally retained on the inner tube, the outer tube having a closed end positionable over the closed end of the inner tube and an open end spaced therefrom, the tapering regions of the interior and exterior layers of the loofah sponge being of a length greater than the length of the tubes whereby the free ends of the interior and exterior layers are positionable between the free ends of the tubes prior to positioning the exfoliating assembly on the rod.

* * * * *